United States Patent
Kono (10) Patent No.: US 11,006,980 B2
(45) Date of Patent: May 18, 2021

(54) SURGICAL MEDICAL INSTRUMENT FOR SPINAL FIXATION

(71) Applicant: Kabushiki Kaisha Hikari, Tokyo (JP)

(72) Inventor: Hitoshi Kono, Tokyo (JP)

(73) Assignee: KABUSHIKI KAISHA HIKARI, Tokyo (JP)

( * ) Notice: Subject to any disclaimer, the term of this patent is extended or adjusted under 35 U.S.C. 154(b) by 17 days.

(21) Appl. No.: 16/287,117

(22) Filed: Feb. 27, 2019

(65) Prior Publication Data

US 2019/0262040 A1     Aug. 29, 2019

(30) Foreign Application Priority Data

Feb. 28, 2018  (JP) .............................. JP2018-034358
Mar. 23, 2018  (JP) .............................. JP2018-055596

(51) Int. Cl.
    *A61B 17/70*    (2006.01)
    *A61B 17/80*    (2006.01)

(52) U.S. Cl.
    CPC ........ *A61B 17/7032* (2013.01); *A61B 17/705* (2013.01); *A61B 17/707* (2013.01); *A61B 17/7044* (2013.01); *A61B 17/7052* (2013.01); *A61B 17/8076* (2013.01); *A61B 17/7007* (2013.01); *A61B 17/7047* (2013.01)

(58) Field of Classification Search
    CPC ............ A61B 17/7032; A61B 17/7044; A61B 17/705; A61B 17/7052; A61B 17/7007; A61B 17/7043; A61B 17/707; A61B 17/7062; A61B 17/7014
    See application file for complete search history.

(56) References Cited

U.S. PATENT DOCUMENTS

| | | | |
|---|---|---|---|
| 5,947,966 A | 9/1999 | Drewry et al. | |
| 5,989,251 A * | 11/1999 | Nichols | A61B 17/7049 606/246 |
| 6,077,263 A | 6/2000 | Ameil et al. | |
| 7,131,972 B2 | 11/2006 | Mazda et al. | |
| 8,617,213 B2 * | 12/2013 | Moore | A61B 17/7052 606/253 |
| 8,956,392 B2 | 2/2015 | Khatchadourian et al. | |
| 9,844,398 B2 | 12/2017 | Daniels et al. | |
| 2003/0032959 A1 | 2/2003 | Yeh | |
| 2012/0004688 A1 * | 1/2012 | Marino | A61B 17/7049 606/251 |
| 2015/0190174 A1 | 7/2015 | McCarthy et al. | |

* cited by examiner

*Primary Examiner* — Ellen C Hammond
(74) *Attorney, Agent, or Firm* — Browdy and Neimark, PLLC (57) ABSTRACT

A medical instrument has a connector configured for being fixed to a spine support, and a rib support connected to the connector and configured for supporting the rib. The medical instrument has a pair of an upper hook and a lower hook provided on the rib support. One of the upper hook and the lower hook is fixed to the rib support so as to be vertically adjustable. The rib support is connected to the connector to be movable in a direction along the rib.

10 Claims, 7 Drawing Sheets

SURGICAL MEDICAL INSTRUMENT FOR SPINAL FIXATION

FIELD OF THE INVENTION

The present invention relates to a surgical medical instrument for fixing a spine.

BACKGROUND OF THE INVENTION

Many types of spinal abnormalities arise from diseases such as a trauma, a tumor, and a degenerated intervertebral disc. Surgical techniques for fixing a part of a spine by the use of surgical medical instruments are widely adopted in spine disease, for example, scoliosis, degenerative disc disease, intervertebral disk displacement, spinal canal stenosis, or other teratogenic diseases.

The surgical medical instruments of related art include a spine support configured for extending along a spine to support the spine, and a rib support configured for extending along a rib to support the rib (see US 2015/0190174 A1). The rib support has a pair of hooks which engages the ribs. The rib support is connected to the spine support. The load applied to the spine is dispersed to the ribs via the spine support and the rib support, and the spine is protected.

Since the rib support of the medical instrument of related art is fixed to the spine support, it cannot move along the ribs. In addition, the pair of hooks of the rib support cannot move in a vertical direction. Because of such a structure, it was often not possible to efficiently disperse the load applied to the spine to the ribs, and it was difficult to engage the hook with the ribs by a minimally invasive surgical procedure.

SUMMARY OF THE INVENTION

Therefore, an object of the present invention is to provide a medical instrument which can efficiently disperse the load applied to the spine to the ribs.

For this reason, the medical instrument according to the invention includes a spine support configured for extending along a spine to support the spine, a rib support configured for extending along a rib to support the rib, and a connector connected to the spine support and the rib support. The rib support has a pair of an upper hook and a lower hook, the upper hook has an upper curved section configured for abutting on an upper surface of the rib, and the lower hook has a lower curved section configured for abutting on a lower surface of the rib. One of the upper hook and the lower hook is fixed to the rib support so as to be vertically freely adjustable. The rib support is connected to the connector to be freely movable in a direction along the rib.

DETAILED DESCRIPTION OF THE PREFERRED EMBODIMENTS

Figure 1:
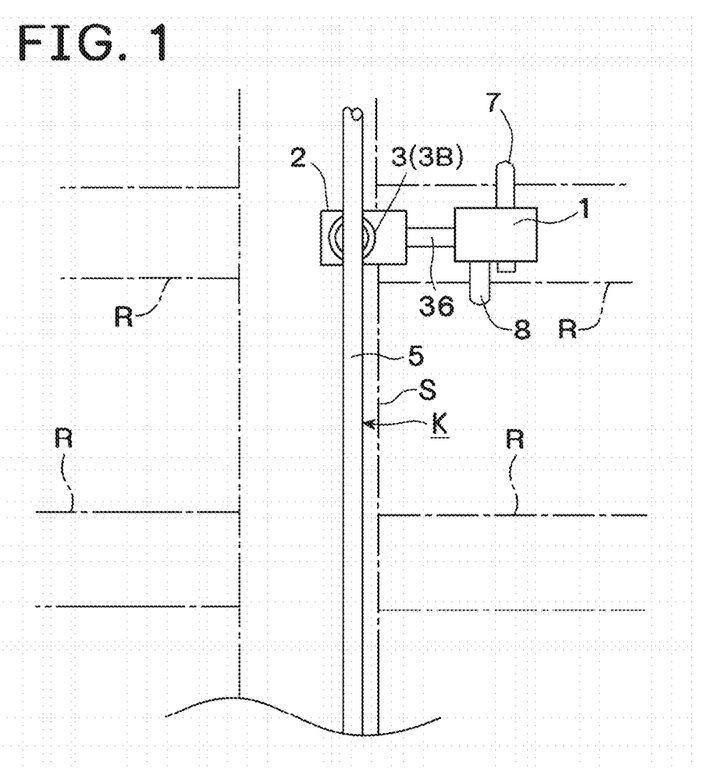
FIG. 1 is a front view of a medical instrument according to the present invention disposed together with a skeleton.

A first embodiment of a medical instrument K for spinal fixation according to the present invention will be described with reference to the drawings. As illustrated in FIG. 1, the medical instrument K of the first embodiment includes a spine support 5 which supports a spine S indicated by a broken line, and a rib support 1 which supports one of ribs R indicated by a broken line. The spine support 5 extends along the spine S in a longitudinal direction or a vertical direction. The rib support 1 extends along the rib R in a lateral direction or a horizontal direction.

The medical instrument K has a connector 2. The connector 2 is preferably fixed to the spine S with a fastener tool 3 such as a tapping screw or a drill screw. The fastener tool 3 can also be formed of bone. The connector 2 is connected to the spine support 5 and the rib support 1 with sufficient strength. The spine support 5 and the rib support 1 are connected to each other in a T-shape or an L-shape via the connector 2.

The T-shape or L-shape medical instrument K can widely support, hold or fix both the rib R and the spine S. This means that the medical instrument K can effectively perform a deformation correction and a curvature correction of the spine S. Further, it means that the load applied to the spine S can be dispersed to the rib R which is spaced apart from the spine S in the lateral direction.

Figure 2:
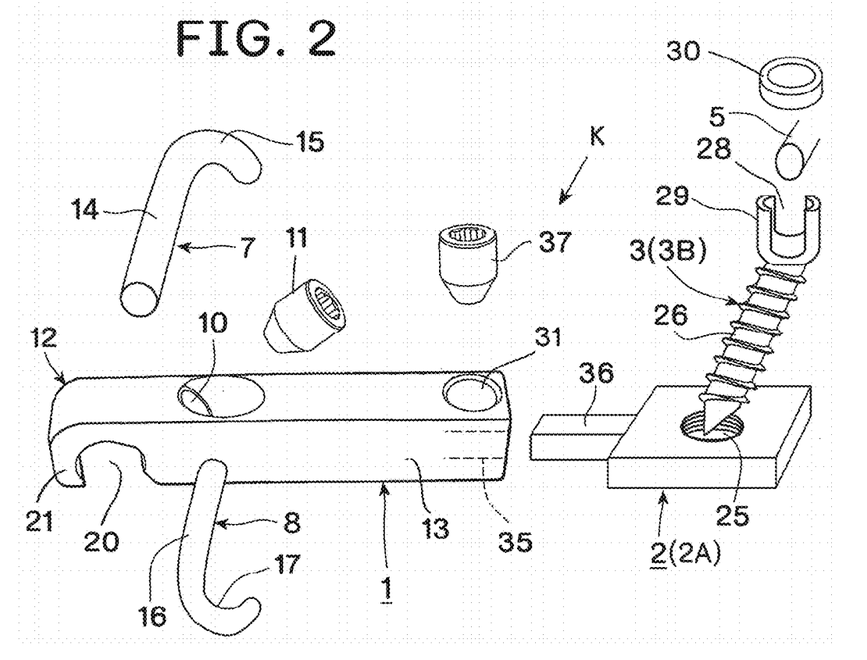
FIG. 2 is a perspective view of the medical instrument.

FIG. 2 illustrates details of the medical instrument K of the first embodiment. The medical instrument K has a connector 2A as a typical example of the connector 2, and a fastener 3B as a typical example of the fastener tool 3. The fastener 3B has a screw section 26 and a U-shaped head section 29. The screw section 26 is screwed into the spine S via a hole 25 of the connector 2A. The spine support 5 is fitted into a groove 28 of the U-shaped head section 29. The ring 30 is threadedly engaged with the outer periphery of the U-shaped head section 29, and the spine support 5 is attached to the fastener 3B.

In the first embodiment, both the connector 2A and the spine support 5 are fixed to the spine by a single fastener 3B. The U-shaped head section 29 is preferably freely rotatable with respect to the screw section 26. The U-shaped head section 29 is also preferably freely bendable with respect to the screw section 26.

Figure 3:
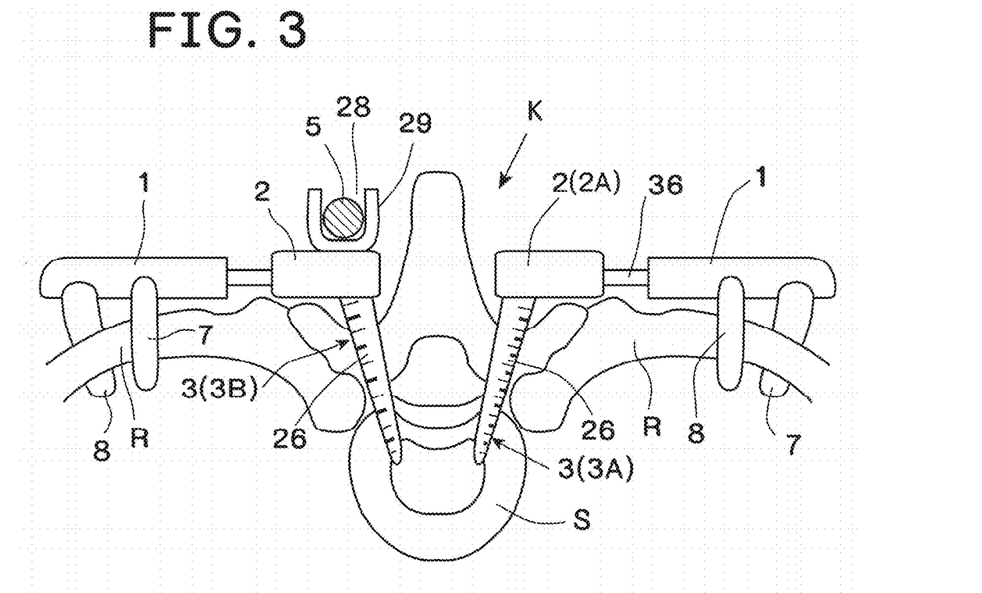
FIG. 3 is a plan view of the medical instrument disposed together with a skeleton.

A left side of FIG. 3 illustrates a relation between the medical instrument K illustrated in FIG. 2 and the spine S and the rib R. A right side of FIG. 3 illustrates a modified example of the medical instrument K illustrated in FIG. 2, in which the connector 2A is fixed to the spine S by a fastener 3A which is another example of the fastener tool 3.

The rib support 1 extends in parallel to the rib R, and has a distal end portion 12 and a base portion 13. The base portion 13 is connected to the connector 2A in a freely movable or adjustable manner. A distance between the base portion 13 and the connector 2A can be adjusted. The connector 2A has a laterally extending insertion section 36, and the base portion 13 has an insertion hole 35 into which the insertion section 36 is inserted. The insertion section 36 is fixed to the base portion 13 by a screw 37 inserted into the hole 31.

The distal end portion 12 is located on the outer side of the base portion 13 or on a side far from the spine. The distal end portion 12 has an adjustable hook 7 and a prefixed hook 8. The adjustable hook 7 has a shaft 14, and a curved section 15 provided at the distal end of the shaft 14. The prefixed hook 8 has a shaft 16 fixed in advance to the distal end portion 12, and a curved section 17 provided at the distal end of the shaft 16.

The adjustable hook 7 and the prefixed hook 8 are preferably identical to each other in shape. The hooks 7 and 8 are attached to the distal end portion 12 in opposite directions to each other. That is, one of the hooks 7 and 8 extends upward from the distal end portion 12, and the other thereof extends downward from the distal end portion 12. The hooks 7 and 8 can be attached to one of the upper part or the lower part of the distal end portion 12. Importantly, the pair of hooks 7 and 8 is attached to the distal end portion 12.

As illustrated in FIG. 2, the shaft 14 of the adjustable hook 7 is inserted into the hook groove 20 of the distal end portion 12 so as to be freely movable in the longitudinal direction. The screw 11 inserted into the screw hole 10 abuts on the shaft 14. The shaft 14 is sandwiched between the screw 11 and a receiving surface 21 and fixed to the distal end portion 12.

Figure 8:
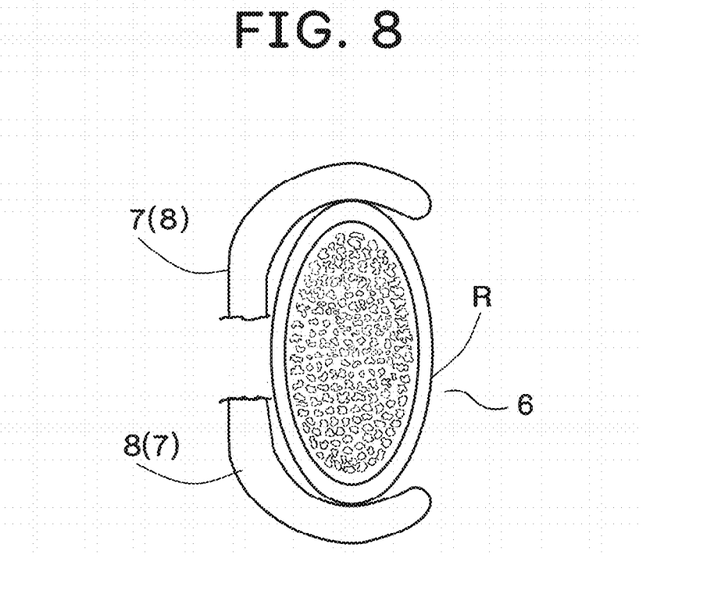
FIG. 8 is a schematic view illustrating the hook of the medical instrument disposed together with ribs.

As illustrated in FIG. 8, the curved section 15 and the curved section 17 have a shape that fits the cross-sectional shapes of the ribs. The curved section 15 supports about half of the upper side or about half of the lower side of the rib, and the curved section 17 supports about half of the lower side or about half of the upper side of the rib. Since the curved section 15 is fixed with respect to the distal end portion 12 by the screw 11 to be freely adjustable in the longitudinal direction, a pair of curved sections 15 and 17 can favorably support the ribs.

When the curved section 15 and the curved section 17 sandwich the ribs from the upper and lower sides, a predetermined gap 6 is set between the distal end of the curved section 15 and the distal end of the curved section 17 (see FIG. 8), so that the distal ends do not overlap each other. Therefore, it is possible to support the rib R from both the upper and lower sides with the curved section 15 and the curved section 17 by a minimally invasive and safe surgical procedure.

When the curved sections 15 and 17 sandwich the ribs from the upper and lower sides, since the rib support 1 is connected to the connector 2A in a freely movable or adjustable manner, the curved sections 15 and 17 can favorably supports the appropriate parts of the rib. As a result, the load applied to the spine S is efficiently transferred to the rib via the spine support 5 and the rib support 1.

The shafts 14 and 16 of the hooks 7 and 8 do not necessarily need to be orthogonal to the distal end portion 12, but rather, the hooks 7 and 8 are appropriately inclined with respect to the distal end portion 12, depending on the shape and angle of the ribs.

Figure 4:
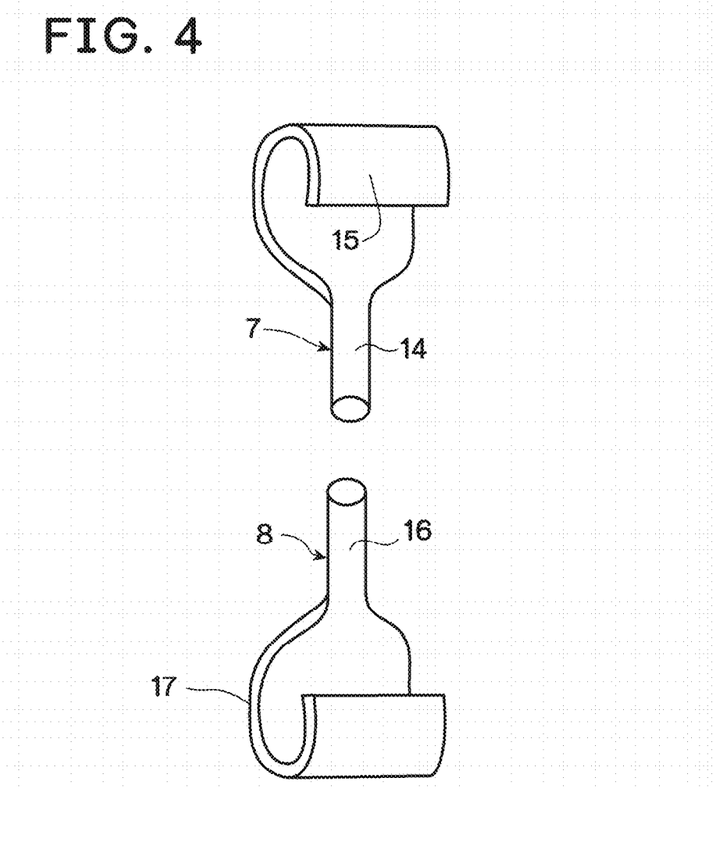
FIG. 4 is a perspective view illustrating a modified example of a hook of the medical instrument.

The curved sections 15 and 17 illustrated in FIG. 2 are formed to have substantially the same thickness as the shafts 14 and 16. In a modified example of FIG. 4, the curved sections 15 and 17 are formed in a curved plate shape extending along the ribs. The plate-like curved sections 15 and 17 can support the rib R in a wide range.

The hooks 7 and 8 can also be manufactured in a desired shape, depending on the situation and shape of a patient's bone. As the hooks 7 and 8, objects with a plurality of different curved shapes or inclination angles may be prepared in advance, and the hooks 7 and 8 of an appropriate shape may be selected at the time of the operation.

Figure 5:
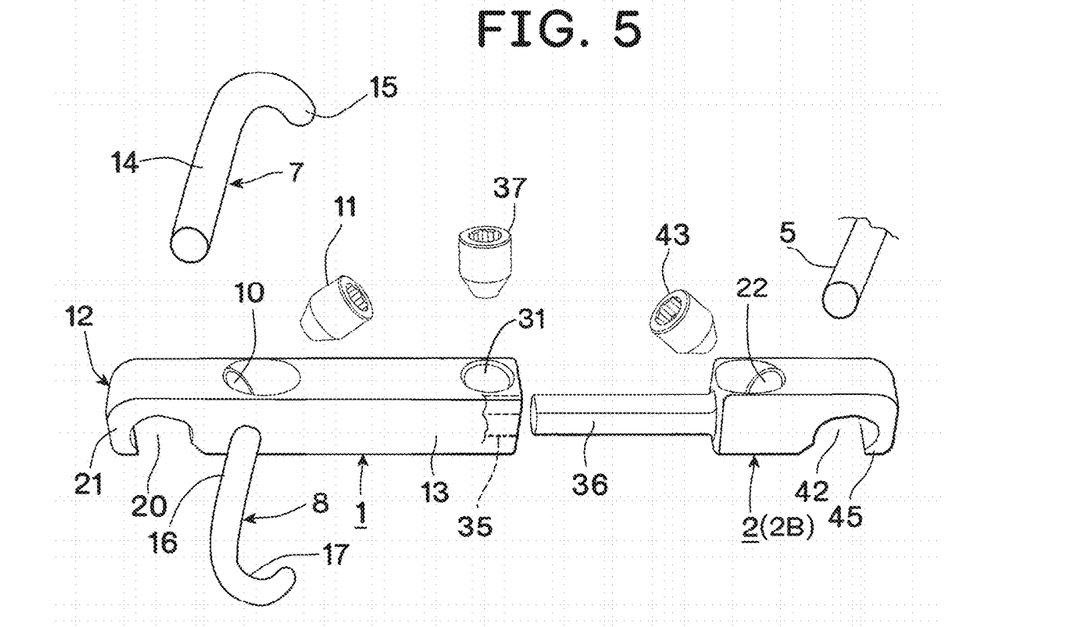
FIG. 5 is a perspective view illustrating a modified example of a connector and a rib support of the medical instrument.

FIG. 5 illustrates a connector 2B which is another modified example of the connector 2. The connector 2B has a support groove 42 similar to the hook groove 20 of the rib support 1. The support groove 42 receives the spine support 5. A screw 43 inserted into the screw hole 22 abuts on the spine support 5. The spine support 5 is sandwiched between the screw 43 and the receiving surface 45, and is fixed to the connector 2B.

In the modified example of FIG. 5, the spine support 5 is fixed to the spine S by a fastener without passing through a connector. The connector 2B is fixed to the spine S via the spine support 5. Naturally, the connector 2B can also be fixed to the spine S by additional reinforcing fasteners or screws, but in the modified example of FIG. 5, by avoiding the use of a fastener with the U-shaped head section 29, the thickness of the connector 2B can be suppressed.

Figure 6:
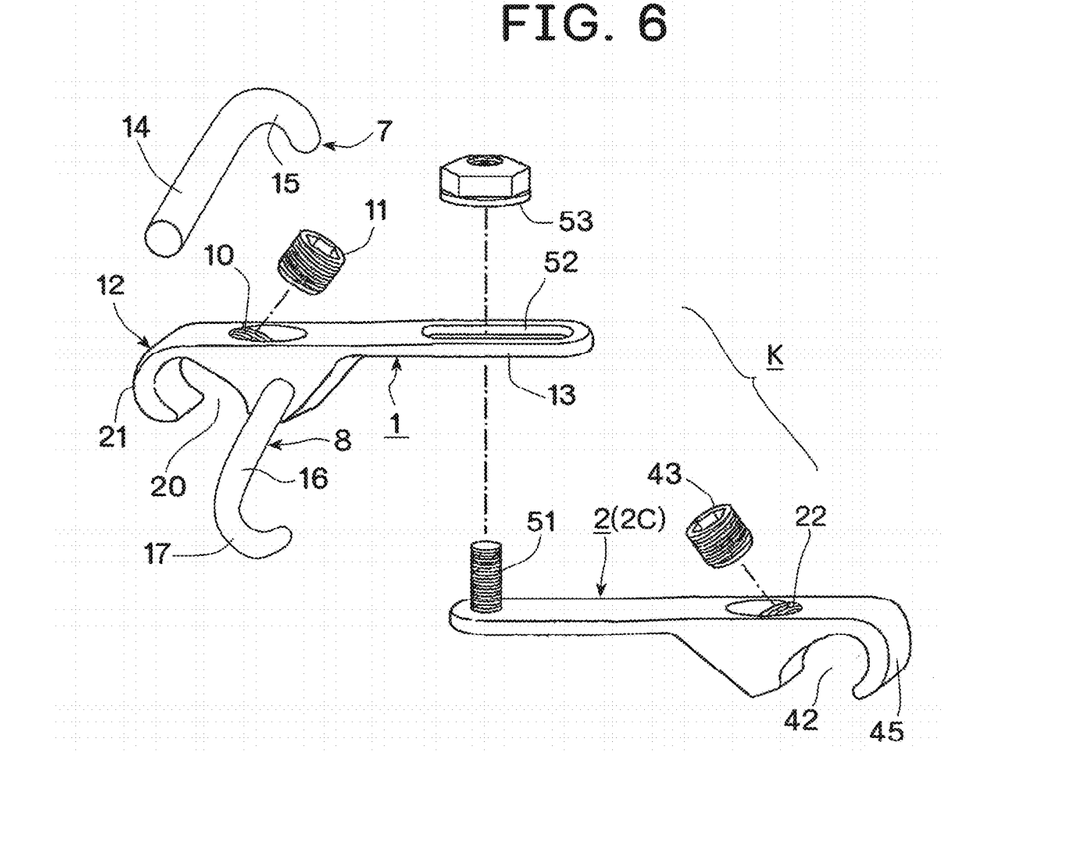
FIG. 6 is a perspective view illustrating another modified example of the connector and the rib support of the medical instrument.
Figure 7:
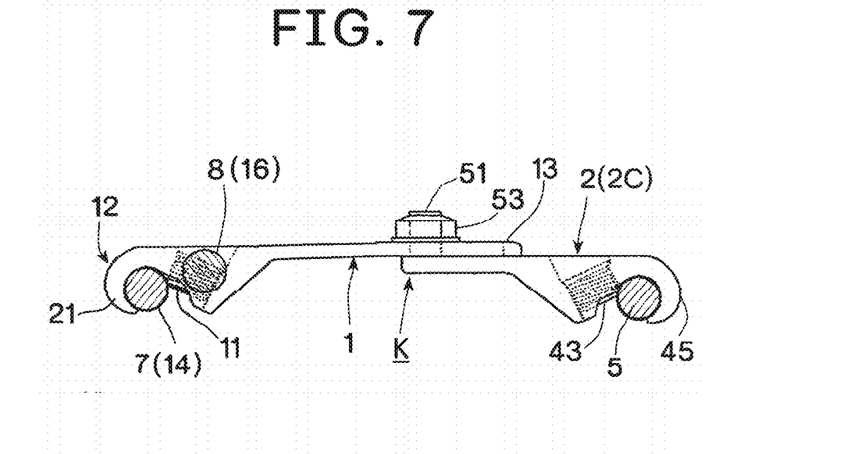
FIG. 7 is a plan view of the medical instrument illustrated in FIG. 6.

FIGS. 6 and 7 illustrate a connector 2C which is still another modified example of the connector 2. The connector 2C has a bolt 51, and the rib support 1 has a lateral slot 52 through which the bolt 51 is inserted. The rib support 1 is connected to the connector 2C by a nut 53 in a freely movable or adjustable manner. In this modified example, since the rib support 1 can be bent around the bolt 51 with respect to the connector 2C, it can easily cope with the curvature of the ribs, and the appropriate curved sections 15 and 17 can further favorably support the appropriate part of the rib.

Figure 9:
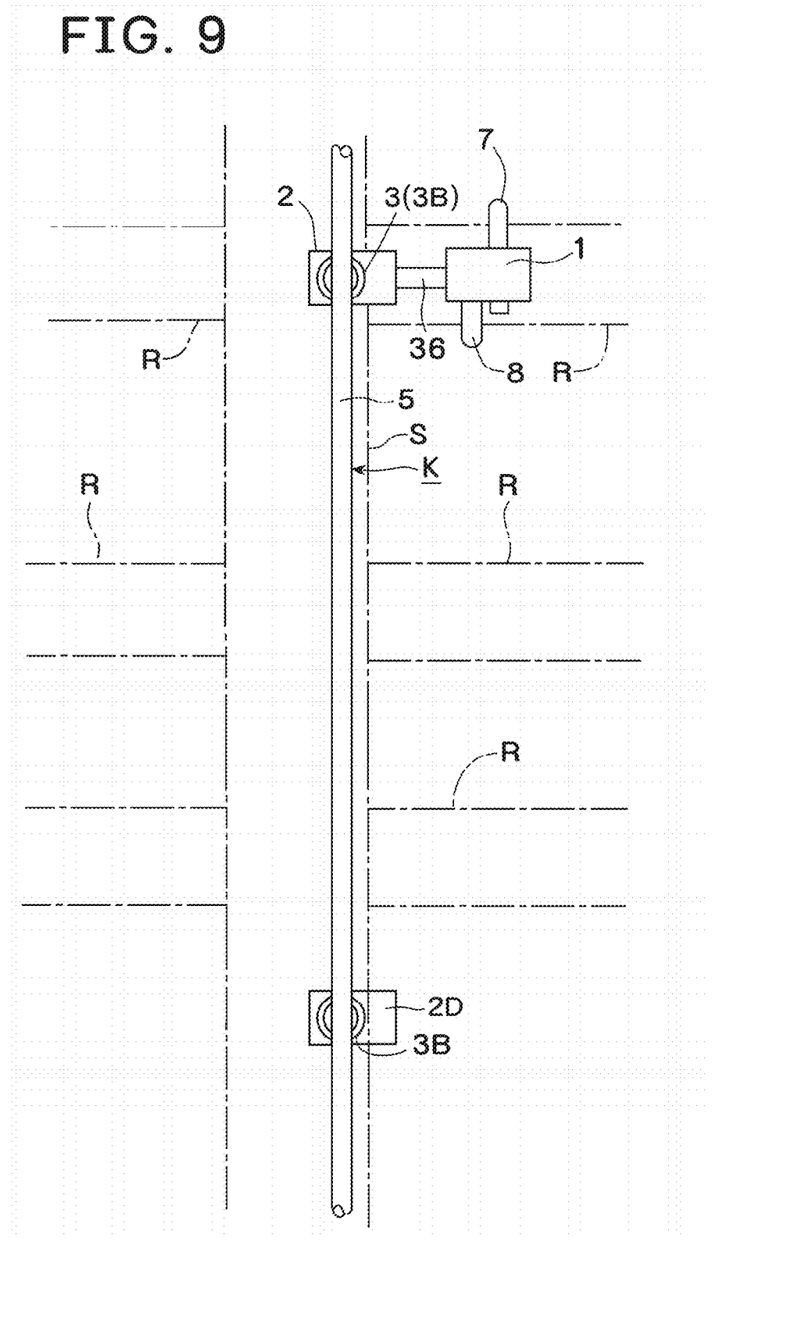
FIG. 9 is a front view illustrating another embodiment of the medical instrument according to the present invention disposed together with the skeleton.

FIG. 9 illustrates a second embodiment of a medical instrument K. The medical instrument K has the long longitudinal spine support 5. A lower part of the spine support 5 is preferably connected to a connector 2D. Since the connector 2D does not support the ribs, it does not include a member corresponding to the insertion section 36 of the connector 2A or the bolt 51. Although one connector 2D is illustrated in FIG. 9, two or more connectors 2D can also be used.

The medical instrument K of the second embodiment can also use the connectors 2A, 2B and 2C, instead of the connector 2D. The connectors 2A, 2B and 2C can be connected to the rib support 1, and it is possible to efficiently support the ribs by the additional rib support 1. When the rib support 1 is connected to the connectors 2A, 2B and 2C, the medical instrument K takes a U shape rather than a T-shape or an L-shape. As a result, the medical instrument K can more effectively perform a deformation correction or a curvature correction of the spine S. Further, the load applied to the spine S can be favorably dispersed by the rib R spaced from the spine S in the lateral direction.

Figure 10:
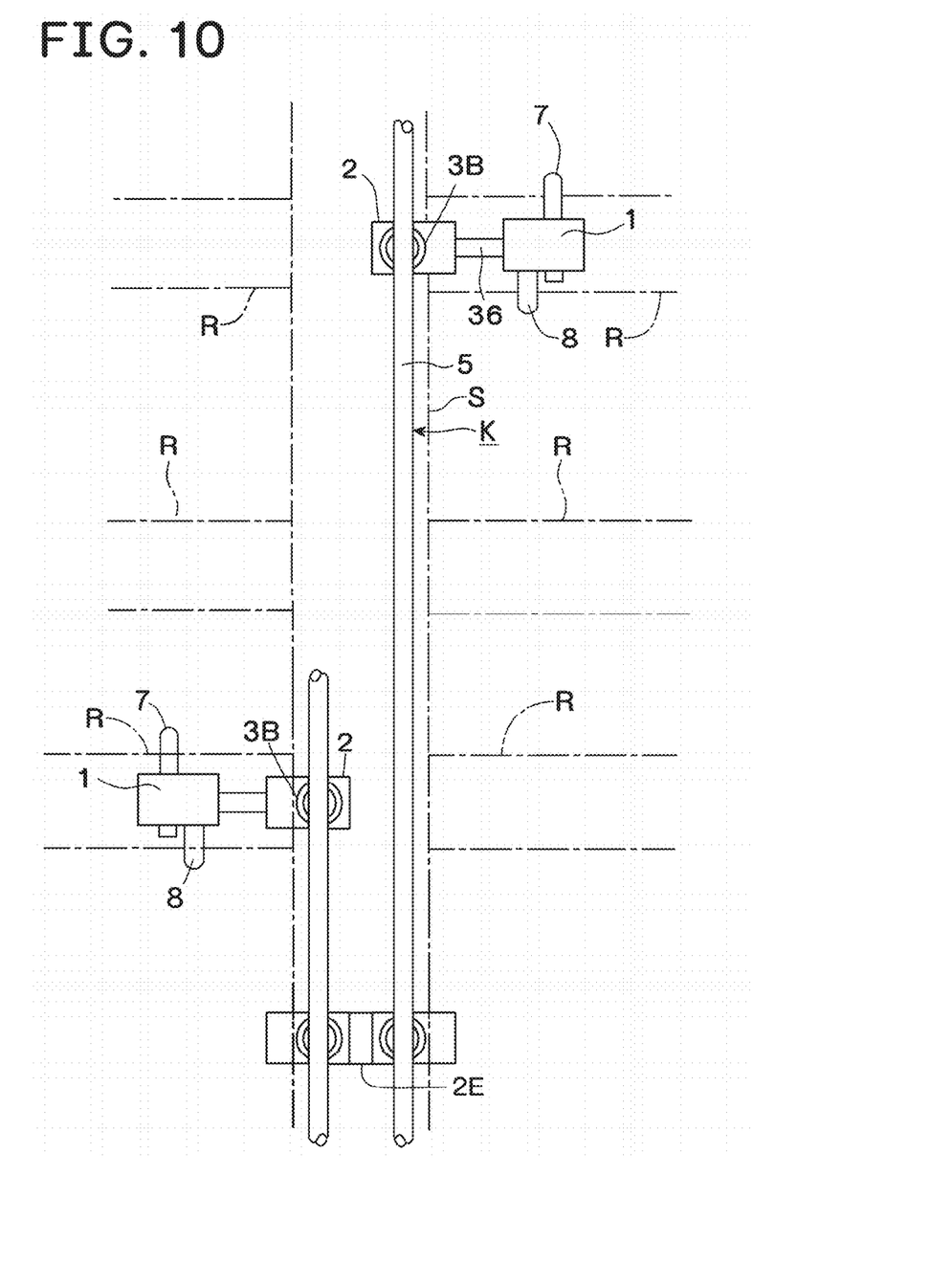
FIG. 10 is a front view illustrating still another embodiment of the medical instrument according to the present invention disposed together with the skeleton.

Depending on the condition of the bone, as in a third embodiment illustrated in FIG. 10, the spine supports 5 are disposed in pairs on the left and right sides of the spine S. The length of the spine support 5 is determined by the condition of the bone. The left and right spine supports 5 need not have the same length. The spine supports 5 arranged side by side are preferably attached to a single connector 2E. The connector 2E preferably includes a pair of support grooves similar to the support groove 42 which can receive the spine support 5. Also, the pair of spine supports 5 and the connector 2E can be fixed to the spine, using the fastener 3B having the U-shaped head section 29.

Figure 11:
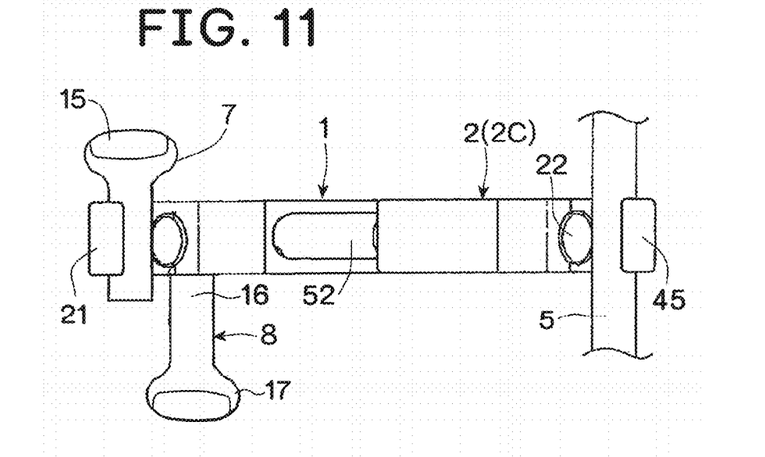
FIGS. 11 to 13 are reference views illustrating one variation of the medical instrument to which hooks of different shapes are attached, respectively.

FIG. 11 illustrates a modified example of the medical instrument K illustrated in FIGS. 6 and 7 as an example. The medical instrument K of FIG. 11 has hooks 7 and 8 provided with the plate-like curved sections 15 and 17 illustrated in FIG. 4.

Figure 12:
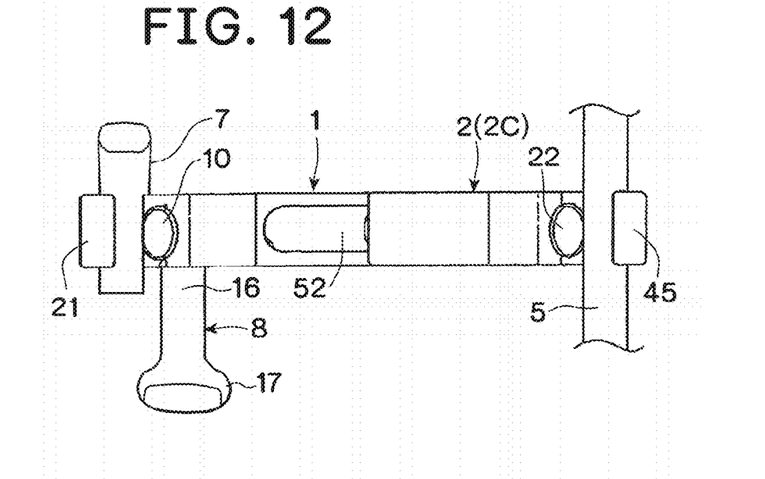

FIG. 12 illustrates another modified example of the medical instrument K illustrated in FIGS. 6 and 7 as an example. In the medical instrument K illustrated in FIG. 12, only a prefixed hook 8 is provided with the plate-like curved section 17.

Figure 13:
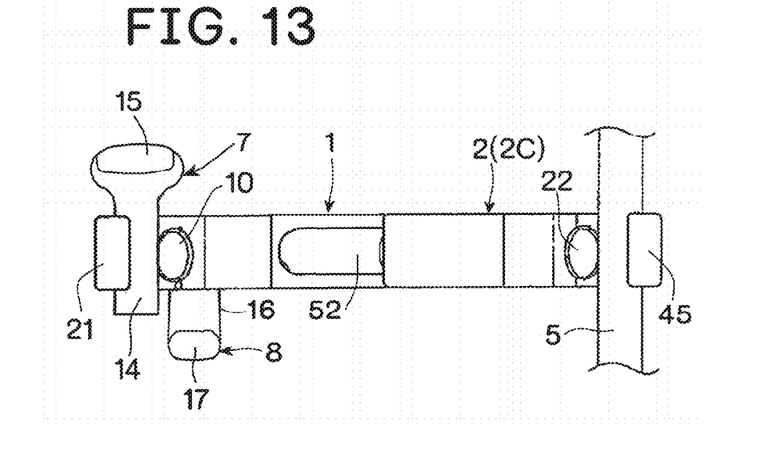

FIG. 13 illustrates still another modified example of the medical instrument K illustrated in FIGS. 6 and 7 as an example. In the medical instrument K of FIG. 13, only an adjustable hook 7 is provided with the plate-like curved section 15.

The thickness of the spine support 5 is appropriately selected depending on the case. It is preferable that the size of the support groove 42 of the connector be appropriately selected depending on the thickness of the spine support 5 to be used.

In the above description, as described in the first to third embodiments and some modified examples of each embodiment, the medical instrument K basically includes the spine support 5 for supporting the spine S, the rib support 1 for supporting the ribs R, and the connector 2 connected to the supports 5 and 1. Depending on the symptoms of the patient, however, the spine support 5 may often not be used. In other words, it is noted that the medical instrument K can also be configured only with the connector 2 fixed to the spine and the rib support 1 connected to the connector 2 in a freely adjustable manner. Furthermore, the spine support 5 is a rod-like component with high general versatility and does not need special machining. Thus, it is noted that the medical instrument K can also be used as a component only provided with the rib support 1 and the connector 2.

A surgical procedure using the medical instrument K will be briefly described.

In the connector 2, the insertion section 36 thereof is inserted through the insertion hole 35 of the rib support 1, and the rib support 1 is temporarily fixed to the connector 2 by the screw 37. The shaft 14 of the adjustable hook 7 is received by the hook groove 20 of the rib support 1, and the hook 7 is temporarily fixed to the rib support 1 by the screw 11.

A patient's back of a state of lying on an operating table is incised, and the spine support 5 is attached to the patient's spine. The spine support 5 may not be used depending on the symptoms of the patient. It is desirable that a part to be incised be near a joint part between the spine S and the rib R.

The curved section 17 of the hook 8 fixed to the rib support 1 is caused to abut on the lower surface of the rib. In this state, while the shaft 14 of the adjustable hook 7 is moved with respect to the hook groove 20, the curved section 15 of the adjustable hook 7 is caused to abut on the upper surface of the rib, and the rib is sandwiched by the pair of hooks 7 and 8. The adjustable hook 7 is completely fixed to the rib support 1 by the screw 11 in an optimum state.

After the hooks 7 and 8 are engaged with appropriate positions of the ribs, the connector 2 is moved with respect to the rib support 1 to adjust the connector 2 to an appropriate position with respect to the spine. Then, the connector 2 is connected and fixed to the spine support 5. In the embodiment illustrated in FIG. 2, the connector 2 is fixed to the spine by the fastener 3B, the spine support 5 is received by the U-shaped head section 29 of the fastener 3B, and then the connector 2 and the rib support 1 are completely fixed with the screws 37 at an appropriate distance. An additional connector 2 can also be fixed to the spine.

Even in the case of using the connector 2B illustrated in FIG. 5 or the connector 2C illustrated in FIG. 6, there is no great difference in the procedure, and after the connector 2B or the connector 2C is connected to the spine support 5, the connector and the rib support are completely fixed.

As illustrated in FIG. 10, in a case where a pair of spine supports 5 is fixed to the spine, the left and right connectors can also be fixed to different thoracic vertebrae, respectively. Further, even when there is a lesion in the lumbar vertebrae under the spine S, the upper part of the spine support 5 can be connected to the rib support 1 via the connector 2, and the lumbar vertebra can also be protected by the lower part of the spine support 5.

The hooks 7 and 8 of the rib support 1 can be caused to abut on the ribs after the connector 2 is fixed to the spine support 5.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the appended claims.

What is claimed is:

1. A medical instrument having a connector configured for being fixed to a spine support extending along a spine to support the spine, and a rib support connected to the connector and configured for extending along the rib to support the rib, the medical instrument comprising:
   a pair of an upper hook and a lower hook provided on the rib support, the upper hook having an upper curved section configured for abutting on an upper surface of the rib, the lower hook having a lower curved section configured for abutting on a lower surface of the rib, one of the upper hook and the lower hook being fixed to the rib support so as to be vertically freely adjustable;
   said rib support is connected to the connector to be freely movable in a direction along the rib,
   wherein the rib support has a hook groove which receives one of the upper hook and the lower hook in a vertically freely adjustable manner, wherein one of the upper hook and the lower hook is fixed to the hook groove by a screw inserted into a screw hole of the rib support.

2. The medical instrument according to claim 1, wherein a gap is provided between a distal end of the upper curved section and a distal end of the lower curved section so that the distal ends do not overlap each other.

3. The medical instrument according to claim 1, wherein the connector is configured for being fixed to the spine with a fastener.

4. The medical instrument according to claim 1, wherein the connector has a receiving groove configured for being able to receive the spine support in a vertically freely adjustable manner.

5. The medical instrument according to claim 1, wherein one or both of the upper curved section and the lower curved section are configured as a plate-like curved section.

6. The medical instrument according to claim 1, further comprising a separate connector configured for being fixed to the spine support.

7. The medical instrument according to claim 6, further comprising a separate rib support connected to the separate connector, the separate rib support being configured for extending along a separate rib to support the separate rib.

8. The medical instrument according to claim 1, wherein a gap is provided between a distal end of the upper curved section and a distal end of the lower curved section so that the distal ends do not overlap each other, the rib support has a hook groove receiving one of the upper hook and the lower hook in a vertically freely adjustable manner, and the connector has a receiving groove configured for being able to receive the spine support in a vertically freely adjustable manner.

9. The medical instrument according to claim 8, further comprising a separate connector configured for being fixed to the spine support, a separate rib support being connected to the separate connector, the separate rib support being configured for extending along a separate rib to support the separate rib.

10. The medical instrument according to claim 1, wherein said spine support comprises a pair of left and right spine supports on both sides of the spine.

\* \* \* \* \*